United States Patent [19]
Hall

[11] Patent Number: 5,892,160
[45] Date of Patent: Apr. 6, 1999

[54] ISOTHERMAL FLOW CONTROLLER FOR AIR SAMPLER

[75] Inventor: Peter M. Hall, McMurray, Pa.

[73] Assignee: SKC, Inc., Eighty Four, Pa.

[21] Appl. No.: 75,103

[22] Filed: May 8, 1998

[51] Int. Cl.[6] .................................................... G01N 1/24
[52] U.S. Cl. ........................................................ 73/863.03
[58] Field of Search ........................... 73/863.03, 861.42, 73/861.52, 861.61, 861.65; 417/20, 43, 44.2

[56] References Cited

U.S. PATENT DOCUMENTS

| | | | |
|---|---|---|---|
| 4,269,059 | 5/1981 | Baker | 73/28 |
| 4,527,953 | 7/1985 | Baker et al. | 417/38 |
| 4,532,814 | 8/1985 | Lalin | 73/863.03 |
| 4,569,235 | 2/1986 | Conkle et al. | 73/863.03 |
| 4,576,054 | 3/1986 | Lalin | 73/863.03 |
| 5,000,052 | 3/1991 | Sipin | 73/863.03 |
| 5,107,713 | 4/1992 | Peck et al. | 73/863.02 |
| 5,163,818 | 11/1992 | Betsill et al. | 417/18 |
| 5,269,659 | 12/1993 | Hampton et al. | 417/12 |
| 5,295,790 | 3/1994 | Bossart et al. | 417/43 |
| 5,325,861 | 7/1994 | Goulding | 73/863.03 |
| 5,365,795 | 11/1994 | Brower, Jr. | 73/861.65 |
| 5,520,517 | 5/1996 | Sipin | 417/44.3 |
| 5,621,180 | 4/1997 | Simon et al. | 73/804.52 |

OTHER PUBLICATIONS

Hughes, "New Laminar Flowmeter", Instruments & Control Systems, vol. 35, pp. 98 to 100, 1992.

Primary Examiner—Robert Raevis
Attorney, Agent, or Firm—William L. Krayer

[57] ABSTRACT

An air or gas sampling device utilizes a small tube calibrated under isothermal conditions. The relationship of pressure at the input end of the tube to flow is plotted and stored in a microprocessor for comparison with pressure monitored during sample pumping. Pulsations in flow caused by the air or gas pump can be neutralized by a damper comprising a small chamber having a diaphragm for one wall.

17 Claims, 7 Drawing Sheets

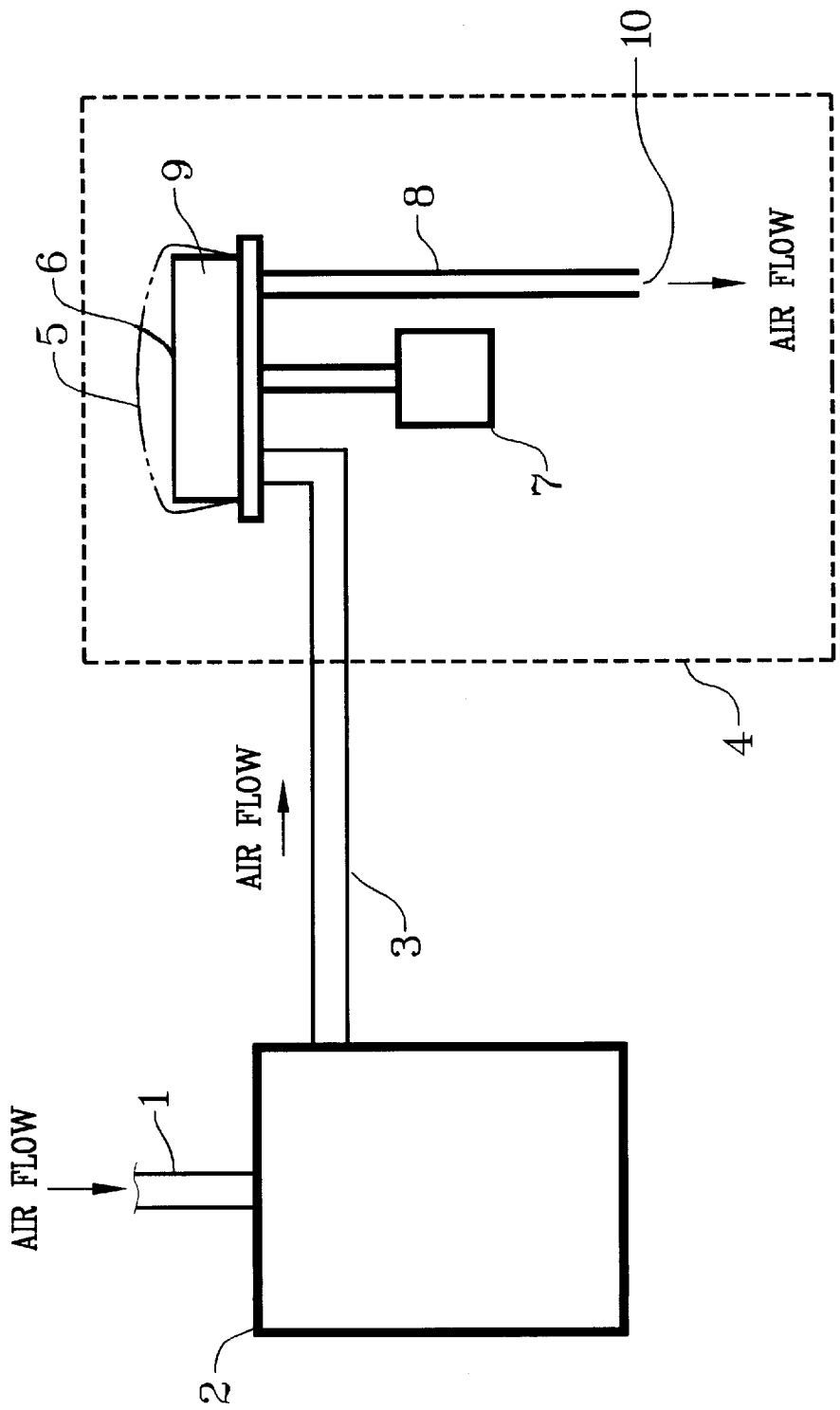

ISOTHERMAL FLOW CONTROLLER FOR AIR SAMPLER

TECHNICAL FIELD

This invention relates to controlling and measuring the air flow in an air sampling device. In particular, it utilizes the concept of isothermal air flow in a flow measuring device, and substantially eliminates the effects of pulsation in the flow of sampled air induced by the strokes of a vacuum pump.

BACKGROUND OF THE INVENTION

It is common practice in air sampling pumps to maintain the air flow at a constant rate independent of buildup in back pressure by direct measurement of the air flow using a suitable sensor, the signal from which is then used to control the speed of the vacuum pump such that constant flow is maintained.

In theory, the volume or rate of air delivered by a small vacuum pump such as is commonly used in a personal air sampler may be controlled and/or measured by employing the known characteristics of the pump in a microprocessor or the like, and comparing the known characteristics to current inputs representing flow, perhaps modifying the inputs by other variables such as outside air pressure or temperature. Various workers in the art have used such approaches to the problem of maintaining accurate air flow readings for use in calculating the concentrations of air contaminants. See, for example, Peck et al, U.S. Pat. No. 5,107,713. These patentees establish a table of values which relate the pump motor's RPM to air flow rates, store them in a microprocessor, and modulate the current pulse width as a function of deviations from the known RPM/flow relationship. Baker et al, in U.S. Pat. No. 4,527,953, vary the current to the pump, and hence its output, also by varying the current pulse width, but as a function of the relative durations of open and closed positions of a differential pressure switch located parallel to an adjustable orifice in the air conduit. Baker et al try to keep the air flow smooth with the aid of an "accumulator" which may be milled or molded into the frame of the pump and covered on one wall with an elastomer sheet (col. 4, lines 17–24). Thus Baker's accumulator is positioned upstream of and removed from his pressure sensor. In an earlier U.S. Pat. No. 4,269,059, Baker places his accumulator between the filter on the intake and the pump.

Pulse width modulation is also used by Hampton et al in U.S. Pat. No. 5,269,659 to control the air pump, this time as a function of pressure differential across a Venturi. Betsill et al, in U.S. Pat. No. 5,163,818, use a programmable computer to calculate flow from a number of variables, and regulate the voltage to the pump motor to maintain a desired air flow rate. In U.S. Pat. No. 5,520,517, Sipin bases the pump motor control on changes in load, sensed by changes in pressure and speed and compared to pump characteristics stored in memory.

Systems relying on known characteristics of pumps assume to one degree or another that the pumps and motors controlling them will not change, but it is known that pumps and motors will wear, lubrication will change with age, gaskets and bearing surfaces will erode or otherwise deteriorate, and various other problems arise to change the response of the pump to a current of a given characteristic.

Also, as observed by Lalin in U.S. Pat. No. 4,532,814, issued Aug. 6, 1985, "(a)ll known pump sampling systems which control flow by adjustment of pump motor speed produce an air flow with relatively high pulse undulations particularly at low flow levels. With a highly pulsed flow it is difficult to set the flow rate." Column 1, lines 59–63. Lalin maintains a steady flow of gas or air to a sample collecting device by providing a supplementary flow of gas or air to the inlet of the pump in response to a signal representing pressure differential across an orifice in the air or gas conduit, thus avoiding controls on the pump motor. Settings for the flow control valve are manually adjusted. The supplementary flow to the inlet of the pump may be taken from the outlet of the pump. See also the continuation-in-part application and U.S. Pat. No. 4,576,054.

Lalin also, in U.S. Pat. No. 5,562,002, disclosed a device for damping the pump pulsations in a reciprocating piston flowtube comprising a diaphragm and a porous member having open channels. The piston drops by gravity to the bottom of the flowtube; the diaphragm is supported by the porous member.

In U.S. Pat. No. 5,000,052, Sipin shows a laminar flow sensing element which comprises a stack of individual flow channels (col. 13, lines 58–68).

None of the above constructions provide a simple device for measuring air or gas sample flow which neutralizes the effect of the back pressure caused by the strokes. The approach of Bossart et al, in U.S. Pat. No. 5,295,790, requires a special laminar flow element such as porous member 21 in a suitable housing, which will "simulate this linear relationship between the flow rate and pressure drop in a portable personal sampling pump."(col. 3, lines 49–51), provided the air flow is maintained at a low Reynolds number. While Bossart et al purport to be able to simulate linear relationship, they do so at the cost of providing the special laminar flow element. The porous element preferred by Bossart and the small orifice used by Baker and others are susceptible to the buildup of particles from the air which can clog up the orifices through which the air must pass, and across which pressure drop is measured. It should be noted that a major use of air sampling pumps of this type is for dust measurement and even with a suitable in-line filter, small particles can still pass into the sensor causing the buildup of changes in calibration over time.

The reader may also be interested in Simon et al U.S. Pat. No. 5,621,180, which uses a coiled capillary tube of 5 cm to 5000 cm length and in internal diameter up to 0.53 mm to control the flow of gas for a predetermined time into an evacuated sample vessel.

SUMMARY OF THE INVENTION

I have developed an air sampling system which uses a tube of large bore in relation to dust particles, such that they will pass through the system rather than clog up small air passageways. This invention utilizes the mathematical relationship that exists between the velocity of a compressible medium (air or other gas) flowing isothermally through a smooth conduit and the pressure drop measured across the two ends of the conduit. The flow can be considered to be isothermal if the energy converted to heat by friction is equal to the heat transferred out of the fluid, i.e. the air maintains constant temperature. This condition can occur in an uninsulated conduit with the same temperature inside and out, with low fluid velocity, i.e. typically up to about three liters of air per minute but including also flows up to 30 liters per minute.

The relationship between flow rate and pressure relies on the medium flowing at a constant rate over the measuring interval, such that a stable pressure reading is obtained. If the flow rate should rise, there is a finite time required for the system to stabilize at the new pressure. This is a problem in sample pump applications, where the reciprocal strokes of a diaphragm pump produce pulses rather than a smooth flow. Most personal air samplers use such a pump, and this invention contemplates its use.

My invention may utilize a pulsation damper which is a small chamber including a diaphragm in one of its walls. The pulsation damper is inserted in the main flow conduit of the air sample exhaust, downstream of the pump. The diaphragm will modify the pulsations of the flow in a predictable manner which permits accurate conversion to flow rate.

BRIEF DESCRIPTION OF THE DRAWINGS

FIGS. 3a, 3b, and 3c are more or less diagrammatic depictions of my invention in an air sampling device.

DETAILED DESCRIPTION OF THE INVENTION

Figure 1:
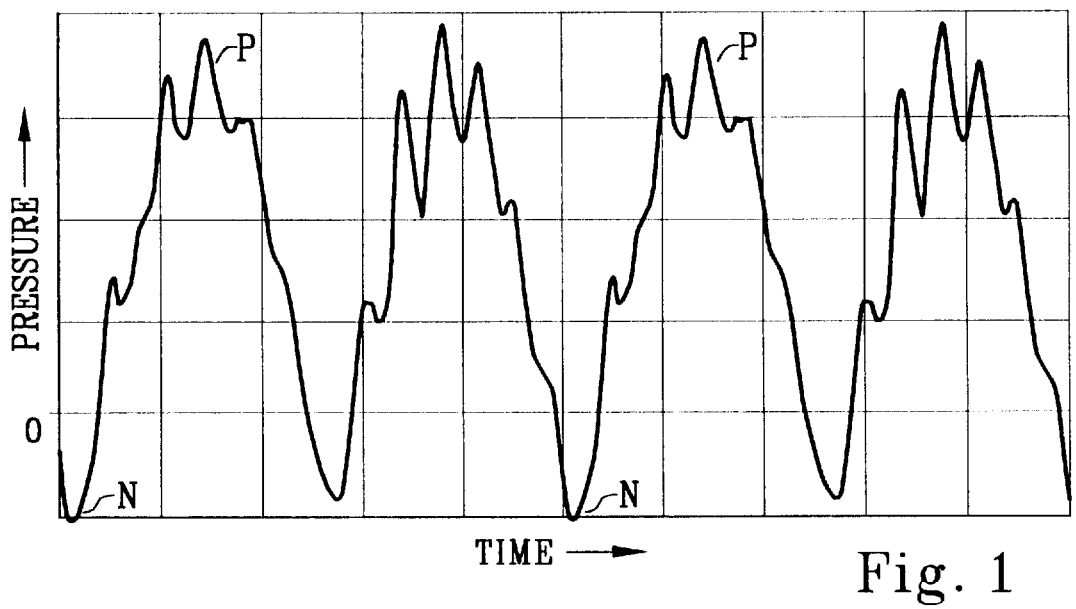
FIG. 1 shows air flow in terms of a pressure profile at the input of a flow sensing device, in particular my isothermal sensor tube.

FIG. 1 illustrates a unitless profile of pressure versus time typically produced by a double diaphragm pump at the input of a flow measuring device, exemplified in this case by my isothermal sensor tube described elsewhere herein. Periodic negative pressures at points N are notable. Such negative pressure points represent back flow, and complicate the accurate calculation of flow. Positive peaks P tend to be sharp but cleaved.

Figure 2:
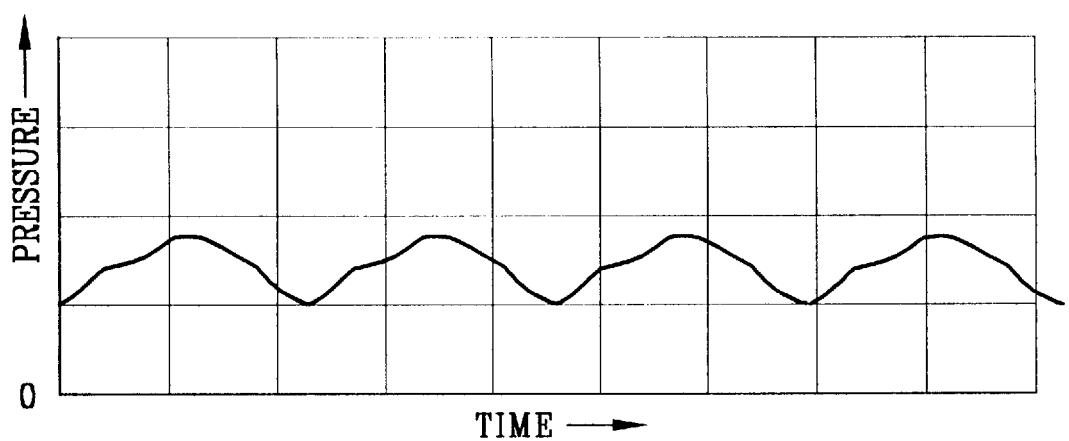
FIG. 2 illustrates the effect of my pulsation damper on air flow.

FIG. 2 shows a plot of pressure versus time similar to that of FIG. 1 where a pulsation damper is connected to the air conduit at the upstream end of an isothermal sensor according to my invention, as illustrated in FIG. 3. It will be seen that no negative pulses are delivered, and the positive peaks P are benign compared to those of FIG. 1. Such a flow pattern is much easier to work with, specifically to project an accurate flow rate, than the pattern of FIG. 1.

In FIG. 3, my invention is shown in place with an air pump 2 having an air intake 1. Air intake 1 for pump 2 comes from one or more sample collecting devices not shown, upstream of air intake 1; the pump 2 draws a vacuum on the sample collecting device or devices. Conduit 3 leads to isothermal sensor tube 8, but I have interposed pulsation damper 9. Pulsation damper 9 is a small chamber into which air may enter from channel 3. Pulsation damper 9 has a diaphragm 6, shown in its normal position; dotted line 5 represents the extended position of diaphragm 6 when it responds to increased pressure in the chamber of pulsation damper 9. In the "gap" between pulses the elastic action of the pulsation damper diaphragm 6 will result in the diaphragm 6 relaxing and this action will tend to maintain the flow of air through the isothermal sensor tube 8. In this way the variation in pressure at the inlet to the isothermal sensor tube 8 as seen by transducer 7 will be diminished as the peaks (see P, FIG. 1) will be reduced and the troughs N "filled in" by the expanding and contracting diaphragm 6.

Connected to pulsation damper 9 is pressure transducer 7 for measuring pressure in pulsation damper 9, effectively the upstream end of isothermal sensor tube 8. The damped version of my air flow meter, comprising the pulsation damper 9, isothermal sensor tube 8, and pressure transducer 7, is shown in the dotted square 4.

Pressure transducer 7 is conventional in that any transducer capable of sensing air pressure and converting it to an electrical signal representative thereof may be used. The analog or digital signal representing pressure at the upstream end of isothermal sensor tube 8 may be used to calculate flow, by itself, or using also either atmospheric pressure at end 10 of isothermal sensor tube 8 (the atmospheric pressure may be measured anywhere in the vicinity) or based on actual sensing of pressure near the end of tube 8 as K shown in FIG. 3a. Flow calculation is accomplished by a microprocessor such as microprocessor 20, shown in FIGS. 5a and 5b, which has stored in its memory the air flow/pressure calibration of the isothermal sensor tube 8.

Figure 3B:
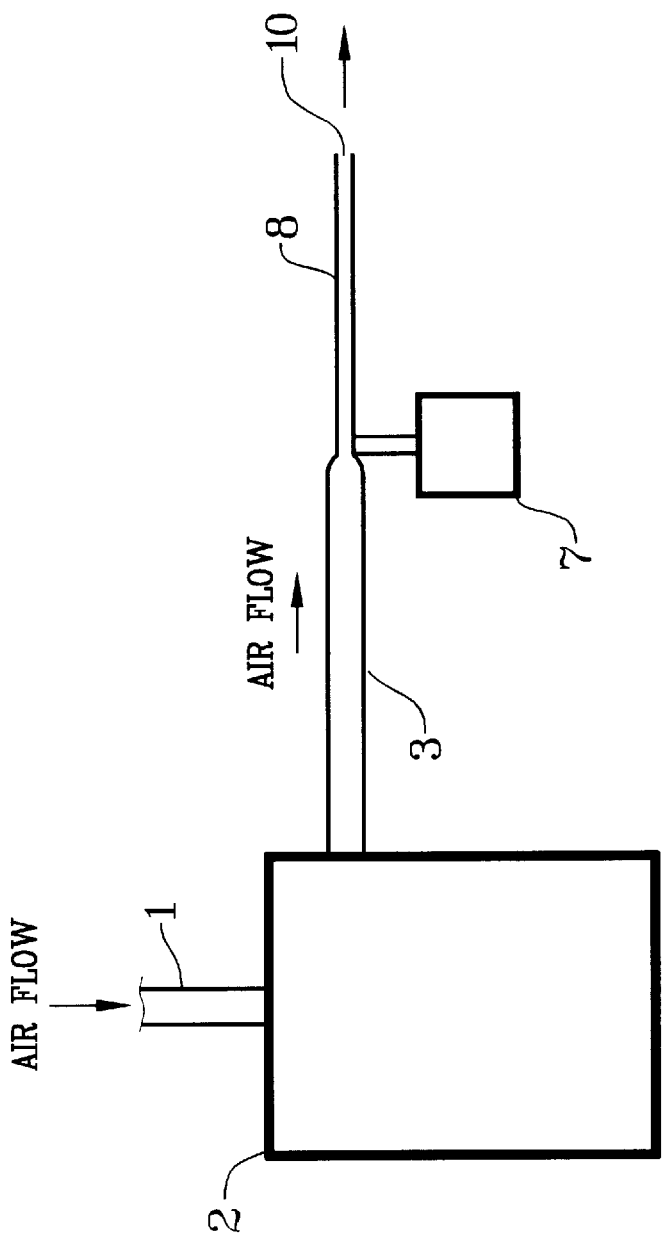

FIG. 3b is a variation of my invention which does not employ pulsation damper 9. Transducer 7 is connected directly to the upstream end of isothermal air tube 8. Electrical output from transducer 7, representing pressure at the upstream end of isothermal sensor tube 8, may be input directly to a microprocessor comparison with a pressure/flow curve stored in memory, derivation of flow, and generation of visible indications of flow, conversion of flow to volume over time, and/or generation of a control signal for the pump as a function of flow. These functions may be performed with or without another pressure input such as a measurement of pressure at downstream end 10 of the isothermal sensor tube 10, or a measurement of atmospheric pressure; the stored curve may take such measurements into account.

Figure 3C:
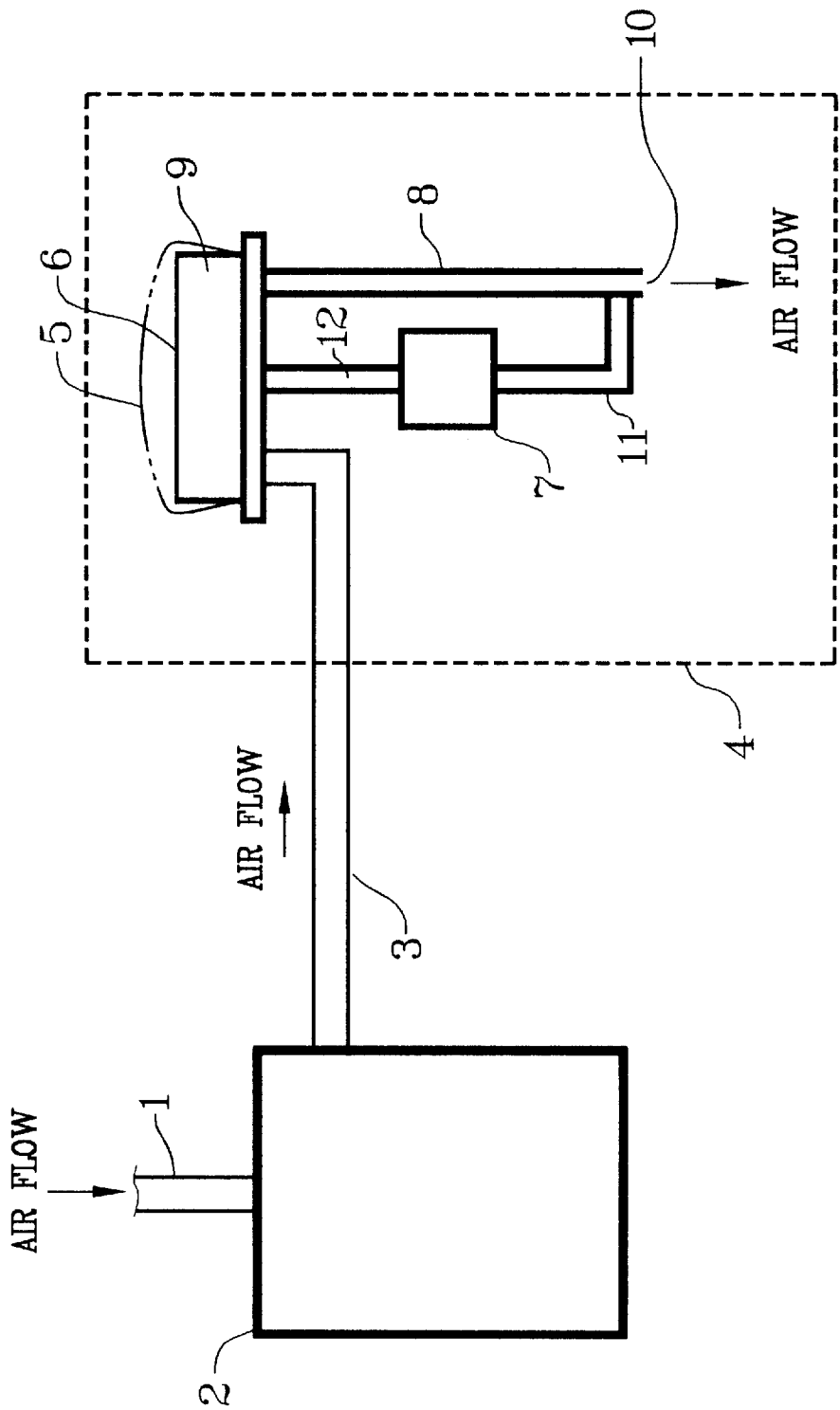

In FIG. 3c, transducer 7 operates as a differential transducer. That is, it receives pressure inputs through connection 11 to the exhaust end of isothermal sensor tube 8 and also through connection 12 to pulsation damper 9, generating an electrical signal as a function of the difference.

Figure 4:
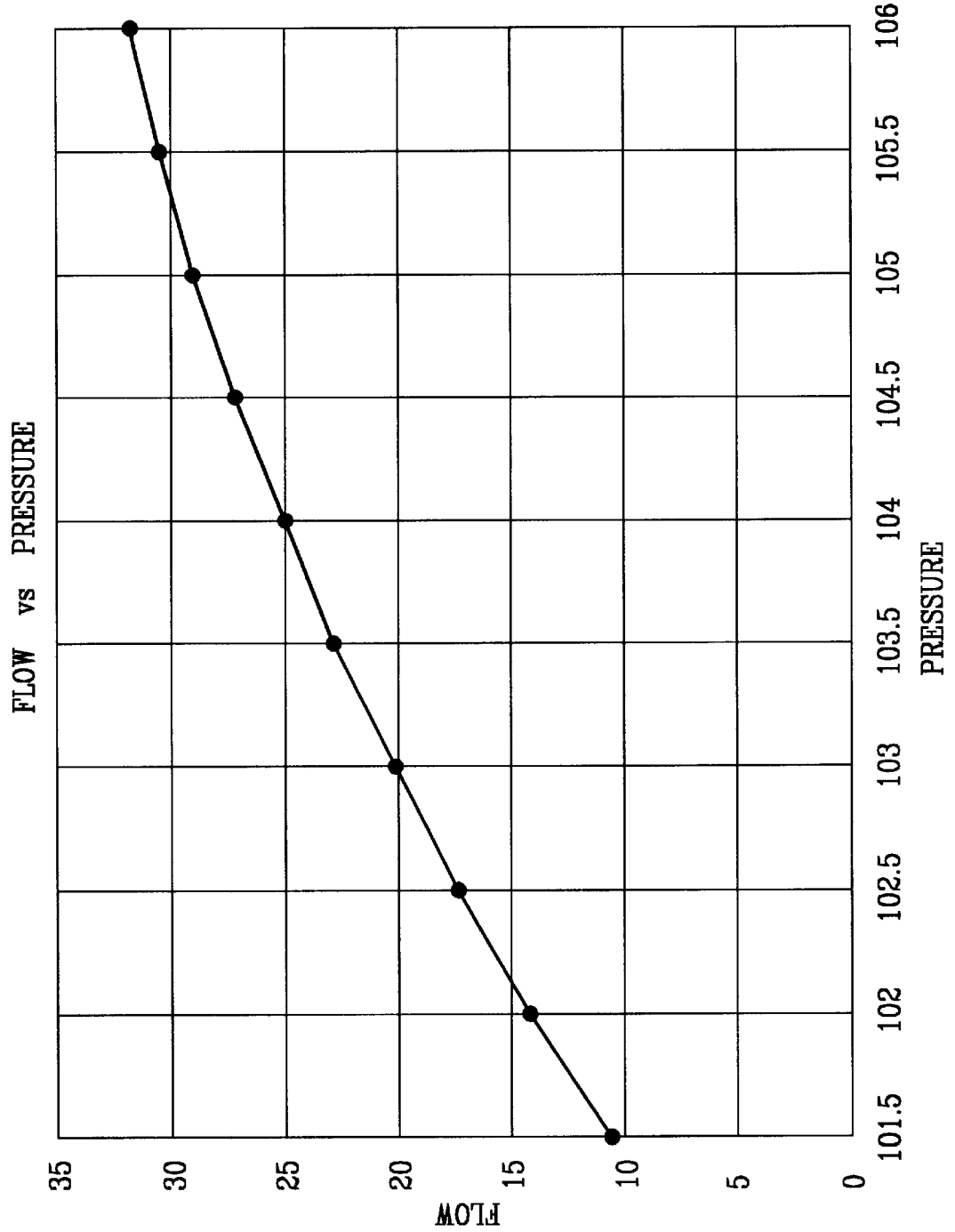
FIG. 4 is an isothermal flow tube curve.

The signal generated by transducer 7, whether representing the pressure in pulsation damper 9 alone, or the difference between pressure in pulsation damper 9 and atmospheric pressure, or the difference between pressure in pulsation damper 9 and measured exiting pressure of isothermal sensor tube 8, may be used to calculate the flow in a microprocessor (see FIGS. 5a and 5b) utilizing a curve such as that of FIG. 4.

In FIG. 4, the characteristics of an isothermal sensor tube such as isothermal sensor tube 8 are shown in terms of pressure and flow. It will be seen that the relationship of pressure and flow is not linear but can readily be used for calibration, computations, and data storage. Isothermal sensor tube 8 is, as explained above, of a large enough internal diameter to pass any and all airborne particulates which might somehow find their way past the particle collection filters or other sample collection means upstream of the pump 2 (see FIGS. 3a, 3b, and 3d).

The Weight Flow rate in an isothermal tube may be described by the following expression:

$$G = \sqrt{C(p_1^2 - p_2^2)} \quad \text{where}$$

G=Weight flow rate;
C=A constant term representing the physical dimensions of the conduit and gas constants;
$P_1$=Pressure measured at the inlet to the isothermal sensor tube, and P₂=Pressure measured at the outlet of the isothermal sensor tube.

By an isothermal sensor tube, I mean a tube of smooth bore having an internal diameter of about 1 millimeter to about 5 millimeters and a length of at least about 10 mm. The length can be conveniently up to about 150 mm. It can also be considerably longer, i.e. 500 mm or more so long as the above described isothermal relationship is present and the tube can be calibrated to a curve such as that of FIG. 4. Preferably, the tube is straight and the internal diameter or bore is of a good consistency—that is, it will not vary more than ±5%.

Figure 5A:
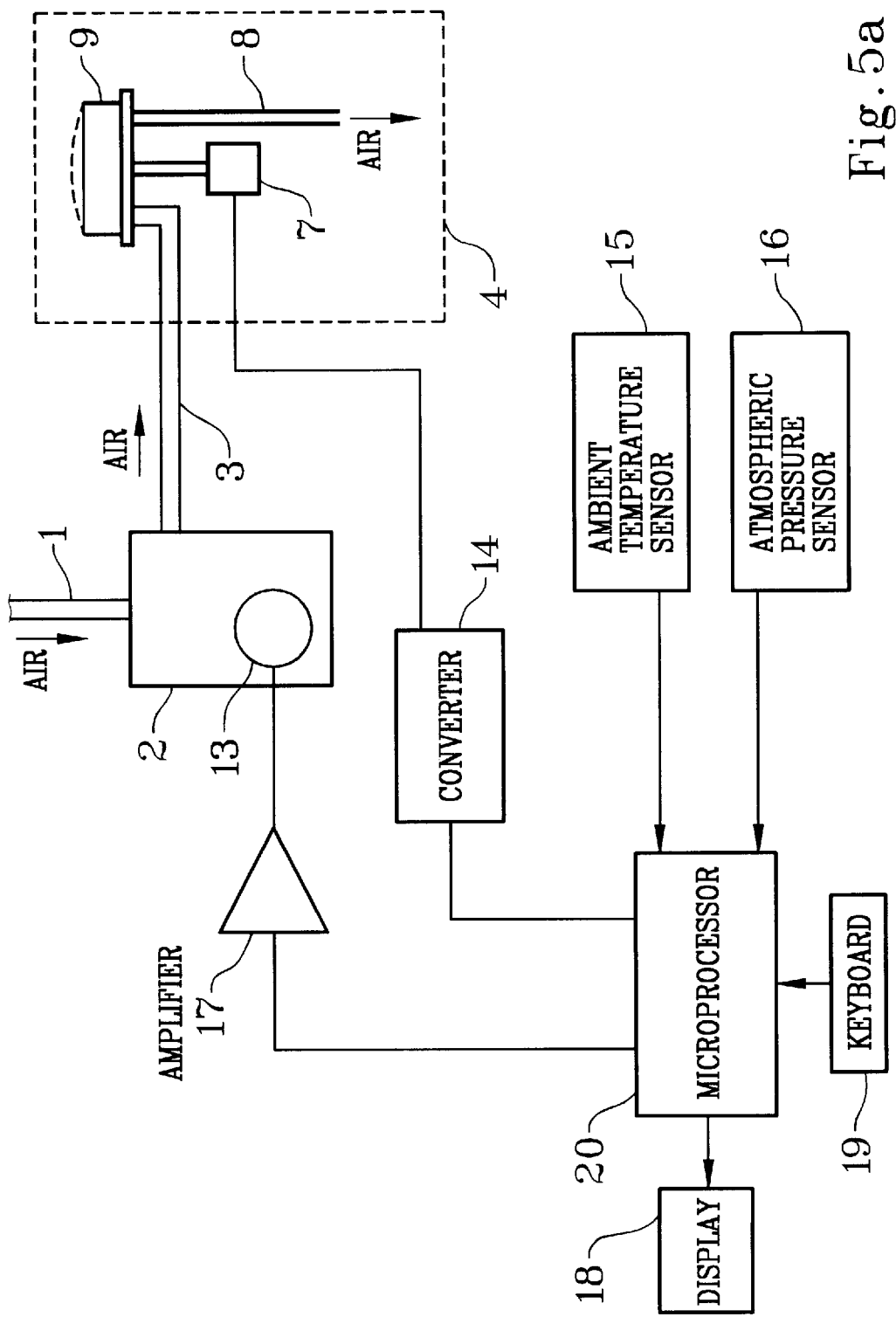
FIGS. 5a and 5b are block diagrams of alternate overall configurations of my invention, differing primarily in the manner of using the microprocessor.

Referring now to FIG. 5a, the microprocessor 20 has programmed into it the airflow versus pressure characteristics for the isothermal sensor tube 8 under various conditions of temperature and atmospheric pressure. The user enters the required flow rate using the keyboard 19 and the microprocessor 20 varies the voltage drive to the pump motor 13 until the expected voltage is received back from the pressure transducer 7, through analog-to-digital converter 14. The microprocessor 20 will then adjust its output to the pump motor 13 to maintain the required flow tinder all loading conditions.

The functions of the microprocessor 20 may include variables (electrical inputs) from temperatures sensor 15 and atmospheric pressure sensor 16. Display 18 may show flow rate, a running volume total, temperatures and pressures as desired.

Figure 5B:
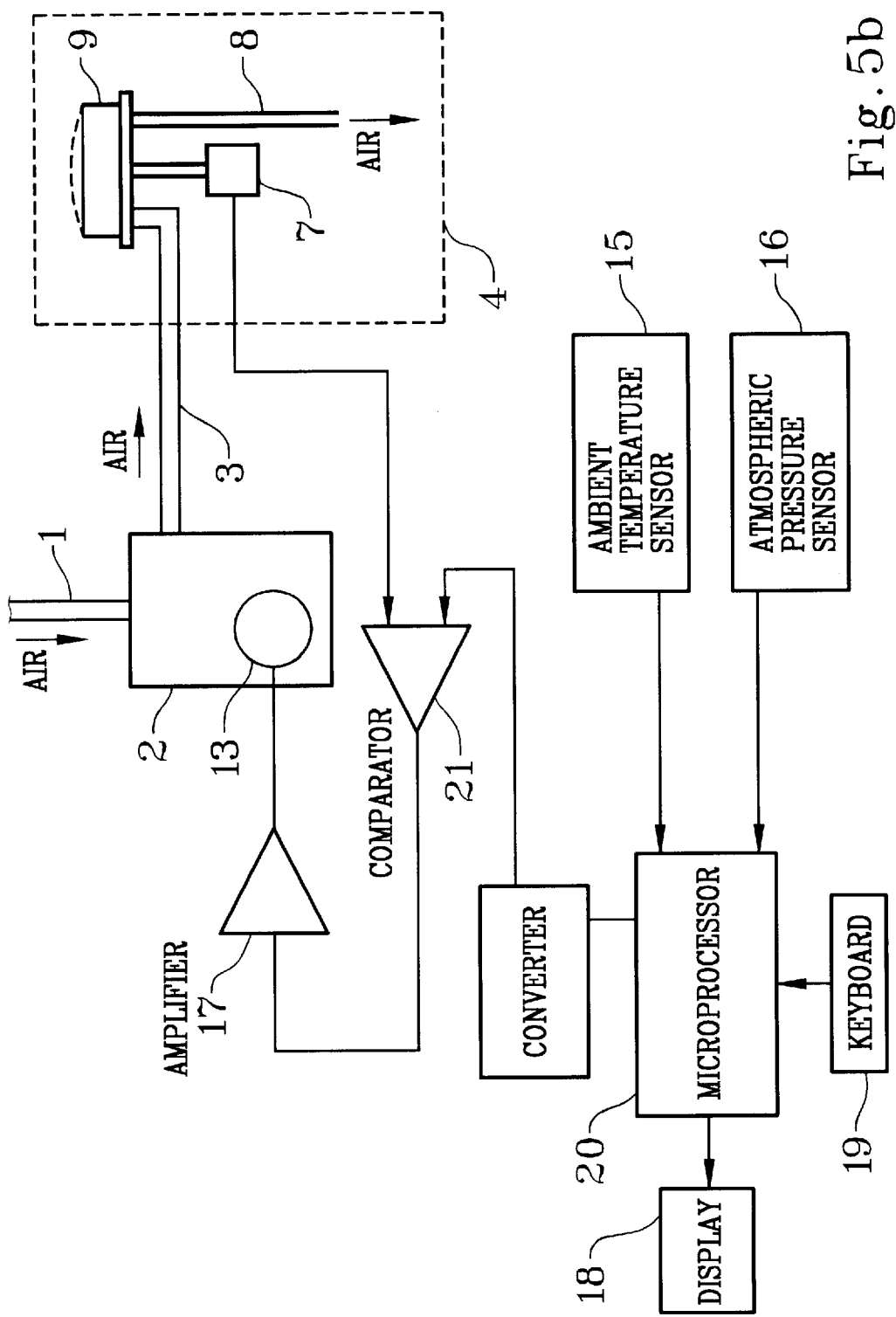

In the version of FIG. 5b, the microprocessor 20 has programmed into it the airflow versus pressure characteristics for the isothermal sensor tube 8 under various conditions of temperature and atmospheric pressure. The user enters the required flow rate using the keyboard 19 and the microprocessor outputs the voltage that it expects the pressure sensor to produce if the airflow is at the correct rate. This voltage is compared with the actual voltage produced by the transducer 7. The analog feedback network comprising comparator 21, drive amplifier 17, pump 2, and transducer 7 adjusts the pump motor 13 until the two inputs of the comparator 21—the microprocessor 20 output voltage and the transducer 7—are equal. In this way the drive to the pump 2 is adjusted to maintain the required flow under all loading conditions.

It should be understood that any of the air flow meter configurations 4 shown in FIGS. 3a, 3b, and/or 3c may be used in either of the layouts of FIGS. 5a or 5b. As has been seen, in any of the versions described herein, the microprocessor 20 may generate not only a signal representing flow, which may be recorded and stored for reference, but may also generate a control signal for modulating the pump motor to assure a steady flow of gas.

It is not necessary to use the pulsation damper in my invention, although it is preferred. Although the kind of pressure profile shown in FIG. 1, without a pulsation damper, is difficult to handle, it is still relatively consistent, and a curve comparable to that of FIG. 4 will be found to be characteristic of an isothermal sample tube even without the pulsation damper. Thus one form of my invention includes apparatus and methods for measuring flow by simply measuring the upstream pressure in an isothermal sensor tube and deriving the flow from a known curve such as that of FIG. 4. The apparatus thus comprises an isothermal sensor tube, transducer means for measuring pressure in the upstream end of said tube and generating an electrical signal representing said pressure, and means for deriving a flow rate from a stored or preprogrammed relationship of pressure to flow rate. The derivation may take into account variations in atmospheric pressure, and/or may utilize a pressure reading at a downstream point in the isothermal pressure tube. The derivation may also take into account the known formula for deriving weight flow rate or the mass flow rate described above.

For most air sampling uses, the pulsation damper is recommended. For most uses, it comprises a chamber having a volume of about 3000 mm³ to about 20,000 mm³ connected to the air exhaust conduit from the pump. It will have a diaphragm or other expandable portion in its wall or top, to absorb pulsations in the air flow as the air is delivered from the pump. The pressure transducer is connected directly to the chamber defined by the pulsation damper.

I claim:

1. Method of measuring gas flow in a gas sampling device including a vacuum pump which generates pulsations in said gas flow comprising passing the exhaust from said pump through a tube having an internal diameter of about 1 mm to about 5 mm and a length of about 10 mm to about 150 mm under substantially isothermal conditions, damping said pulsations in said gas flow in a pulsation damper located at the upstream end of said tube, measuring the pressure at the upstream end of said tube, and deriving gas flow from a predetermined relationship between gas flow in said tube under substantially isothermal conditions and upstream pressure in said tube.

2. Method of claim 1 wherein said pump is a dual diaphragm pump.

3. Method of claim 1 wherein the downstream pressure is also measured at the downstream end of said tube, and said downstream pressure is also used to derive said gas flow from said predetermined relationship between gas flow in said tube under substantially isothermal conditions and said upstream pressure in said tube.

4. Method of claim 1 wherein said gas is air and atmospheric pressure is also measured in the vicinity of said gas sampling device and said atmospheric pressure is also used to derive said gas flow from a predetermined relationship between air flow under substantially isothermal conditions and said upstream pressure in said tube.

5. Method of claim 1 wherein said tube is substantially straight, its bore is substantially smooth, and its internal diameter is substantially constant with variations no more than about 5%, whereby said gas flow is determined according to the formula $$G = \sqrt{C(p_1^2 - p_2^2)} \quad \text{where}$$

G=weight flow rate, C is a constant representing the physical dimensions of said bore and the physical characteristics of said gas, $p_1$ is pressure at said upstream end of said tube, and $p_2$ is pressure at the downstream end of said tube.

6. Method of claim 1 wherein said pulsation damper comprises a diaphragm.

7. Method of claim 1 including adjusting said vacuum pump as a function of gas flow.

8. Method of claim 1 wherein the pressure measurement taken at said upstream end of said tube is taken in said pulsation damper.

9. Method of claim 1 including adjusting said vacuum pump as a function of gas flow.

10. Apparatus for measuring gas flow in a gas sampler including a vacuum pump having a gas exhaust, said apparatus comprising a tube connected to said gas exhaust, a pulsation damper at the upstream end of said tube, a transducer for sensing pressure in said pulsation damper and generating an electrical signal as a function of said pressure, and means for deriving gas flow from a comparison of said electrical signal to a predetermined relationship of pressure at said upstream end of said tube to isothermal gas flow in said tube.

11. Apparatus of claim 10 wherein said transducer is also for sensing pressure at the downstream end of said tube and generating an electrical signal also as a function of said downstream pressure.

12. Apparatus of claim 10 wherein said pulsation damper comprises a chamber having a diaphragm on at least one wall thereof.

13. Apparatus of claim 10 wherein said means for deriving gas flow is a microprocessor.

14. Apparatus of claim 13 wherein said microprocessor includes means for generating a signal as a function of gas flow for adjusting the output of said vacuum pump.

15. Apparatus of claim 10 including a separate transducer for sensing atmospheric pressure and generating an electrical signal as a function thereof, and wherein said means for deriving gas flow derives gas flow also from said electrical signal.

16. Apparatus of claim 10 wherein said tube is at least 10 mm long and has an internal diameter of about 1 mm to about 5 mm.

17. A gas flow measuring device comprising (a) a tube at least about 10 mm long having an internal diameter of about 1 mm to about 5 mm varying no more than about 5% throughout its length (b) a transducer for measuring gas pressure at one end thereof and generating an electrical signal representative of said gas pressure and (c) means for deriving air flow from said signal representative of said pressure as a nonlinear function thereof.

* * * * *